United States Patent [19]

Monafo

[11] 4,088,754
[45] May 9, 1978

[54] WATER-SOLUBLE CERIUM (CEROUS) SALTS IN BURN THERAPY

[75] Inventor: William W. Monafo, St. Louis, Mo.

[73] Assignee: Research Corporation, New York, N.Y.

[21] Appl. No.: 663,052

[22] Filed: Mar. 2, 1976

[51] Int. Cl.$^2$ ............... A61K 33/24; A61K 31/625
[52] U.S. Cl. ........................... 424/131; 424/DIG. 13; 424/229
[58] Field of Search ..................... 424/131, DIG. 13

[56] References Cited

U.S. PATENT DOCUMENTS 3,761,590   9/1973   Fox ..................................... 424/228

OTHER PUBLICATIONS

*J. Bact.* 54:417, 1947.

*Primary Examiner*—Frederick E. Waddell
*Attorney, Agent, or Firm*—Cooper, Dunham, Clark, Griffin & Moran

[57] ABSTRACT

Water-soluble cerium salts and compositions containing the same have been found to be useful in the treatment of burns, such as by the application of an aqueous solution of a water-soluble cerium salt to the burn surface. Particularly useful in burn therapy is the combination of a water-soluble cerium salt, such as cerous nitrate, with silver sulfadiazine.

6 Claims, No Drawings

WATER-SOLUBLE CERIUM (CEROUS) SALTS IN BURN THERAPY

This invention relates to the treatment of burns in animal and man. More particularly, this invention relates to compositions useful in burn therapy. Still more particularly, this invention relates to compositions suitable for use in burn therapy, the compositions being applied topically or directly to the burn surface.

The history of burn therapy or treatment is replete with examples of transient enthusiasm for drugs or methods of wound management which putatively prevent or suppress bacterial growth so as to promote wound healing and decrease the high mortality but which, in any event, have proved to be worthless or even harmful. The spectrum of materials suggested or employed for burn treatment ranges from pigeon dung to tannic acid and beyond. A prominent recent example is the sulfonamide mafenide introduced in 1966, which is now being abandoned because of its toxic effect and because its routine use on large burns leads to lethal superinfections.

The mafenide experience also points up the hazard attending the use of experimental animal "burn models" to screen agents of potential clinical utility; mafenide, a clinical failure, is highly efficacious in the animal model; silver nitrate, after 10 years, still efficacious and safe clinically, has little or no therapeutic effect in the animal model. There are likely several reasons for such apparent inconsistencies. It remains inescapable that, until satisfactory animal models are developed, valid conclusions about the efficacy and safety of burn wound treatments can only be reached by clinical trials.

Silver sulfadiazine is currently widely employed in the treatment of burns and the results of this medicament in burn therapy have been valuable and well received, see U.S. Pat. No. 3,761,590 disclosing the use of silver sulfadiazine in burn therapy. The disclosures of U.S. Pat. No. 3,761,590 are herein incorporated and made part of this disclosure.

The heterogeneous microflora that regularly colonizes large burn wounds causes most of the morbidity and the mortality that attends these injuries. Despite major improvements in supportive care, death is frequent from burns of more than 40% of the skin surface, is regular when the wounds cover ⅜ to ¾ of the skin and is essentially invariable in larger injuries. Better ways of safely suppressing or, ideally, eliminating bacterial and, to a less important extent, fungal colonization of the wound during the days or weeks required for removal of the eschar and permanent wound closure are necessary if a significant reduction in mortality from burns is to occur.

It is an object of this invention to provide compositions useful in burn treatment.

It is another object of this invention to provide a useful burn treatment or therapy.

It is yet another object of this invention to provide improved compositions useful in the treatment of burns and techniques or methods of preparing and employing the same.

How these and other objects of this invention are accomplished will become apparent in the light of the accompanying disclosure. In at least one embodiment of the practice of this invention, at least one of the foregoing objects will be achieved.

It has been found that water-soluble cerium salts, particularly water-soluble cerous salts, e.g. cerous nitrate, and compositions containing the same, particularly compositions containing cerous nitrate and silver sulfadiazine, are useful in the treatment of burns.

The metal cerium is the lightest but one of the "lanthanons" or "rare earth" group elements comprising atomic numbers 57 through 71. Cerium is actually fairly plentiful in nature, is relatively inexpensive and readily available. Cerium exists in both trivalent and tetravalent forms. The water-soluble trivalent nitrate salt $Ce(NO_3)_3.6H_2O$ forms a colorless aqueous solution.

The salts of cerium and other lanthanons are known to possess bacteriostatic properties in low cencentration, see Burkes and McCleskey, *J. Bact.* 54: 417, 1947. In the 39 bacterial species they studied, cerous nitrate inhibited growth in concentrations on the order of 0.004m. The concentration of silver in clinical use in burns ($AgNO_3$) and AgSD (silver sulfadiazine) is 0.03M. The precise biochemical level at which cerium and other lanthanons exert their bacteriostatic effect is unknown. Cerium is poorly absorbed from the gastrointestinal tract and experimentally has negligible toxicity by that route. After intravenous administration cerium is excreted principally by the liver and kidney. More than 50% of the administered dose in rodents or guinea pigs is accumulated by the liver and thereafter rapidly excreted in the feces. The toxicity of intraperitoneally injected cerium varies somewhat with the salt used but in guinea pigs and mice it varies from 37 to 109 mg/kg body weight. Heretofore, however, although the metal cerium has significant in vitro toxic effects on a variety of bacteria and fungi, its clinical use as an antiseptic in burns or other open wounds had not been investigated or suggested. As indicated hereinabove, the chemical and pharmacological properties of cerium indicate it should have little toxicity when used topically. Confirmatory thereof, cerous nitrate applied topically for several weeks to open excised or thermal wounds in rats caused no preceptible toxicity.

Scrupulously monitored clinical trials on cerium (the cerous salt, cerous nitrate) in burn patients were carried out. In these trials 60 patients were treated and the observed mortality was more than 45% less than what would have been expected had silver compounds alone been the primary topical antiseptic employed.

Thirty-three men, 15 women and 12 children age 15 years or less were treated; their age range was 6 months to 92 years. Most of the patients had flame burns, but 3 had electrical injuries. All but three patients were first seen within 12 hours following injury. No bacteria or fungi were recovered from the wounds before the cerium nitrate treatment was begun in 24 patients. In other words, the wound treatment was therapeutic in 36 patients, prophylactic in 24.

Shock was treated or prevented by the intravenous administration of saline solutions, the principal constituent of treatment being a hypertonic lactated saline solution. Escharotomy, fasciotomy or endotracheal intubation were performed when necessary using the usual clinical indications. Burned limbs were elevated. Intravenous fluid administration was usually unnecessary after 48 hours; intravenous cannulas and indwelling urinary catheters were removed as soon as possible, at which time their tips were cultured. High protein-high caloric diets were initiated as soon as ileus had resolved. Tube feedings were used as necessary. Standard intravenous hyperalimentation was not used because of its risks, although several patients were given significant quantities of isotonic or hypotonic amino acid solutions through peripheral veins as a dietary supplement. Most patients were given penicillin during their hospitalization as a precaution against streptococcal or staphylococcal lymphangitis.

Dirt, debris and loose skin were systematically removed from the wounds initially; hirsute burned areas were shaved. Quantitative wound cultures from at least one area, including that of the deepest burn, were obtained on admittance and daily thereafter in most patients. No patient had fewer than three quantitative wound cultures weekly.

Several methods were used to deliver the cerium nitrate to the wounds.

(1) Wet Soaks

Loosely woven gauze bandages saturated with an 0.9 percent saline solution that also contained $Ce(NO_3)_3 \cdot 6H_2O$ in concentration of 0.04M were applied and rewet with the same liquid at two hourly intervals.

(2) Cerium Nitrate Cream

In most patients, the wounds were simply covered with a generous layer of a water-soluble cream base that contained $Ce(NO_3)_3 \cdot 6H_2O$ in concentration of 0.05M and the wounds were then covered with a dry cotton dressing.

(3) Cerium Nitrate-Silver Sufadiazine Cream

Eight patients were treated with silver sulfadiazine cream to which had been added a concentrated solution of $Ce(NO_3)_3 \cdot 6H_2O$ in the ratio of 52.2 ml of the solution to 2400 grams of the water-soluble or water-dispersible cream base, so that the final concentration of cerium in the cream was 0.05M, while that of the silver sulfadiazine was slightly less than the original 1 percent. This cream was also covered by a dry cotton dressing. In a few patients with massive injuries, the cream dressings were additionally saturated at 2 hourly intervals with the aqueous cerium nitrate-saline solution to inhibit the evaporative water loss through their large wounds.

The dressings were changed daily, or at 8 to 12 hour intervals if there was significant soilage of them or if intensive local debridement seemed desirable in order to more rapidly prepare the wound for skin grafting. Visible cream was carefully removed before reculturing the wound surfaces. Tub baths were not used regularly because of the hazard of general contamination of extensive wounds from feces or from small but heavily contaminated wound loci.

Tangential excision of obvious subdermal wounds was carried out routinely nearly always in the first 5 days post injury. This resulted in removal of most of the eschars promptly without significant blood loss.

Split thickness skin grafts were applied as soon as a wound area of significant size was free, or nearly free, of eschar, using either general anesthesia (often Ketamine), local infiltration anesthesia (Lidocaine) or local hypothermic (ice) analgesia for the donor sites. Sheet grafting was used wherever possible. No "mesh" grafts were used.

Apart from those infections being intensively monitored on the wound, indications for the use of systemic antibiotics other than penicillin were based on a combination of the usual clinical and cultural criteria for the diagnosis of pulmonary, urinary or other infections. Antibiotics, usually Oxacillin, Methacillin, or aminoglycosides were administered to some patients with systemic but non-specific manifestations of significant infection, such as toxic delirium, adynamic ileus, etc., in whom the wound itself was judged to be the cause of the systemic illness. In those patients, antibiotic selection was based on in vitro sensitivity tests to the predominant wound flora.

The patients generally fared well. The cerium nitrate, whether applied as a cream or a liquid, did not cause burning or stinging of consequence; in no patient was discomfort sufficient to stop the treatment. Cutaneous allergy was not a significant problem; the cerium nitrate was stopped in one patient because of a cutaneous eruption; although in a few others transitory rashes were observed, they disappeared despite the continued topical use of cerium nitrate. The wounds generally appeared clean and were odorless. Obvious necrotizing wound infection was not encountered. Skin grafts took readily and dermal wounds epithelialized at their anticipated rates. In several instances, dermal burns healed more rapidly than anticipated. The incidence of skin grafting was not excessive, substantiating the impression that the topical treatment did not impede spontaneous healing. Donor sites invariably healed promptly beneath the cerium dressings. Hospital stays were modest in length and about the same as those observed during the past decade when silver nitrate or silver sulfadiazine was the mainstay of treatment. Cerium nitrate does not stain wounds, skin or linen and, when used in liquid form, can be prepared in physiologic saline solution so that mineral leaching from the wounds — a significant disadvantage when silver nitrate soaks are used — is not a problem.

Cerium salts form a characteristic dry precipitate on the surface of dead tissue that varies from off-white in the thinnest eschars to yellow or light green in thicker ones. Residual flecks of cerium salts on granulations can readily be removed using the convex aspect of a curved hemostat as a blunt scissor or by gentle wiping with a wet sponge. Cerium salts are stainless. Granulating surfaces exposed to cerium for weeks accept skin grafts readily.

Seven of the 60 patients died. Five of the deaths occurred within the first week; with one exception, these were elderly patients with large, deep burns who died of cardiovascular complications. The single death among the patients, with moderately large injuries, was from pulmonary embolus.

One patient died of sepsis, but in retrospect, this death was likely preventable, as it resulted from septicemia due to *Beta-hemolytic streptococcus*. This patient was one of the few patients not given precautionary penicillin from the outset.

The observed mortality was compared to the data of Bull, see Lancet, 1133, Nov. 20, 1971, whose patients were treated topically with silver nitrate. As Table I shows, there were six fewer deaths observed than expected, an apparent reduction in the mortality rate of more than 45%. The Chi-square test did not permit rejection of the null hypothesis at the usual significance level — not surprisingly in view of the modest size of the present series. Nevertheless, the data do show that the observed mortality is at least equivalent to that attending the topical use of silver salts; stated otherwise, the probability that the apparent fall in mortality was not due to random variation is about 75%.

TABLE I

| % BSA Burn | # Patients | # Deaths Observed | # Deaths Predicted from Probits* |
|---|---|---|---|
| 1-19 | 32 | 0 | 1.1 |
| 20-39 | 16 | 1 | 3.3 |
| 40-96 | 12 | 6 | 8.7 |

TABLE I-continued

| % BSA Burn | # Patients | # Deaths Observed | # Deaths Predicted from Probits* |
|---|---|---|---|
| Total | 60 | 7 | 13.1 |

$P < 0.3 > 0.2$ - not statistically significant
*Bull's Mortality Probit Chart, Lancet, 1133, November 20, 1971

Bacteriological wound monitoring was close. Nearly 2400 quantitative wound cultures and more than 100 blood cultures were obtained from the 60 patients. One hundred twenty eight additional cultures were taken of sputum, tracheal aspirates, urine or other sources. 27% of the wound cultures were sterile. Wound cultures that yielded only the commensals *Bascillus subtilus* or *S. albus*- organisms of dubious pathogenicity on burn wounds, were also counted as positive.

The wound flora was comprised predominantly, but not exclusively, of Gram-positive bacteria and especially of *Staphylococcus aureus*. This was so even in the patients with the largest wounds.

The cultures from each patient were also examined with respect to the interval post injury at which they were obtained. The principal wound inhabitant during each interval was determined individually by assessment of both the recovery rates and density of individual species. *Staphylococcus aureus* was again predominant, at least during the first 35 days, irrespective of other considerations.

*Pseudomonas aeruginosa* and yeasts were recovered relatively infrequently and were never predominant.

Both the heterogeneity and density of the flora tended to peak during the first two weeks following injury, which was when clinical episodes of sepsis, which were rare later, nearly invariably occurred — an observation underlining the pivotal role of the wound and the importance of effective suppression of its flora. After the first two weeks, fewer types of bacteria tended to be present and their density generally was less: these findings of course correlated with progressive wound closure by both spontaneous healing and by skin grafting.

Bacteremia was found in seven patients. In one patient, a child, who was first seen after her wounds had been treated elsewhere with silver sulfadiazine for 6 days, bacteremia due to *Staphylococcus aureus* — also recovered from her wounds — was present on admittance before the topical treatment with cerium nitrate was begun. She recovered.

Gram-positive bacteria predominated in the blood as they did on the wounds. The single instance of bacteremia due to the Gram-negative *Klebsiella* was obtained pre-terminally in the patient mentioned hereinabove who was dying of overwhelming Streptococcal sepsis. There were no blood cultures obtained after the first two hospital weeks that yielded growth.

One case of methemoglobinemia (2.4 gm %) was observed; this presumably was due to the systemic absorption of nitrite formed by bacterial reduction of the topically applied nitrate anion, as reported previously in patients treated with silver nitrate. The methemoglobinemia resolved with 24 hours after withdrawal of the cerium nitrate; the cerium nitrate treatment was resumed in the same patient 4 days later and applied subsequently for more than 30 days without recurrence of the methemoglobinemia.

A complete blood count and blood levels of urea, calcium, phosphoric uric acid, total protein, albumin, glutamo-oxalic, transaminase bilirubin and alkaline phosphatase were determined at weekly intervals. Analysis of these results did not indicate that renal, hepatic or hematological toxicity attributable to the topical wound treatment had occurred.

The results in the eight patients treated simultaneously with cerium nitrate-silver sulfadiazine are of special interest. All three patients with burns of 1-19% BSA so treated had organisms recovered prior to treatment, seven of nine wound cultures being positive. Of the 40 subsequent wound cultures obtained 23, or 57% yielded no growth during the next 14 days. The same trend was evident in those patients with the most severe injuries who were treated with the cerium nitrate-silver sulfadiazine cream simultaneously. The incidence of negative wound cultures was always twice or more than that obtained in patients with similar injuries who were treated with cerium alone — irrespective of the interval post-injury; there was a corresponding tendency toward a less dense and more homogeneous wound flora in those patients. The clinical course of these patients was extraordinarily benign, see the following specific case reports.

Case No. 1 — A 50-year old electrician sustained deep thermal burns that covered 75% of his skin when arcing occurred from an electrical panel on which he was working in a small, closed room. His clothing ignited and extrication was impossible for several minutes because of the flames and smoke. He was seen within four hours after the injury; constricting eschars of the torso and all four limbs were released by incision. Endotracheal intubation was necessary after 24 hours; tracheostomy was performed the following day because of voluminous tracheo-broncheal secretions that could not be cleared through the endotracheal tube. Diagnostic fiberoptic bronchoscopy showed hyperemia and the presence of carbon particles consistent with a diagnosis of inhalational injury of moderate degree. (The tracheostomy was removed after 14 days.) Cultures of the wound on admittance grew *E. aerogenes* in density $10^3/cm^2$ of wound surface. The topical wound treatment was with cerium nitrate-silver sulfadiazine cream from the outset. Tangential excision of areas of the deepest injury was carried out at the bedside on two occasions during the first week. During the third week, autologous skin grafting was begun using the scalp, feet and buttocks as primary skin donor sites. Additional, minor tangential excisions were performed as necessary just prior to the application of the skin grafts. Donor sites and grafts were dressed for several days with dressings impregnated and kept wet with 0.04M $CeNO_3$ aqueous solution until the grafts were adherent after which the treatment with cerium nitrate-silver sulfadiazine cream was resumed. All the skin grafts took well. Nine grafting procedures were done; about two-thirds of the original wound eventually required skin grafting. Anemia necessitated the administration of 6750 ml of erythrocytes during his hospital stay. A course of systematic gentamycin was given during the second and third weeks because of profuse tracheal-bronchial secretions that grew a variety of Gram-negative bacteria. Bacterial wound density reached $10^6$ on only one occasion, that on the 7th day. The same species — Group D Streptococcus was recovered from his blood the following day. He was discharged from the hospital on the 77th day, at which time the wounds were virtually closed.

The clinical course was notably smooth. Signs of systemic illness were few and those that occurred appeared to be related to the inhalational injury and secondary bacterial tracheo-bronchitis rather than to the wound itself. 69 of 142 wound cultures (49%) yielded no growth.

This middle-aged patient had massive injury. Bacteriological control of the wounds, although imperfect, was nevertheless highly satisfactory and easily exceeded that previously attained using silver compounds alone in patients with comparable injuries.

Case No. 2 — A 17-year old girl sustained deep thermal burns which, by conservative estimate, covered 75% of her skin when her paper costume was ignited by a classmate. The burns were particularly deep on the face, neck, hands and arms. There was mild inhalational injury confirmed by endoscopy, which was confined to the supraglottic area, but tracheal intubation was never necessary. The wounds were treated beginning within 6 hours after the injury with the cerium nitrate-silver sulfadiazine cream. These dressings were additionally kept saturated with 0.4M aqueous cerium nitrate solution in an effort to impede vaporizational water loss through the large wounds. Pre-treatment cultures grew Pneumococci in density $4.8 \times 10^2/cm^2$ wound surface from her face. Tangential excisions of the areas of the deepest burn were carried out at the bedside on three occasions during the second postburn week. Her course was complication-free except for the usual aregenerative anemia which required the transfusion of 4275 ml of packed erythrocytes. Autologous skin grafting was begun during the third postburn week. Five grafting procedures were necessary in order to cover the large subdermal wound, which comprised about 80% of the total. Graft take approached 100% in each instance. Fresh grafts were treated topically with the aqueous cerium nitrate solution alone until the grafts were adherent as in Case No. 1.

Forty-three of 56 wound cultures (86%) were negative. Staphylococcus aureus was recovered in density of $10^7/cm^2$ wound surface from a culture of the face during the first postburn week. The same species was simultaneously being recovered from her pharynx. Thereafter, however, no wound culture exceeded $10^3/cm^2$ wound surface in density. She was discharged from the hospital on the 59th day.

As in Case No. 1, the prevention of dense wound colonization essentially eliminated signs of systemic illness. The clinical course was exceptional, clearly exceeding expectations based on considerable previous experience with the use of silver compounds alone.

Qualitatively, the microflora of cerium-treated wounds appears to differ strikingly from that observed during the past 10 years when the silver compounds 0.5% silver nitrate and 1% silver sulfadiazine were in regular use. During 1966-1973, Gram-negative bacteria were predominant on the wounds. During 1975, after the introduction of cerium, Gram-positive bacteria, especially Staphylococcus aureus were the principal wound inhabitants.

This observation led to the trial of simultaneous topical treatment with both cerium nitrate and silver sulfadiazine reported hereinabove. Although only eight patients have been treated, five of them had deep and extensive injuries and were monitored closely. A striking increase in the percentage of sterile cultures as compared to the results obtained with cerium alone was immediately obvious as was the decline in average wound bacterial density.

In summary, cerium nitrate has a potent antiseptic effect in human burn wounds, especially against Gram-negative bacteria and fungi. Pseudomonas aeruginosa was recovered relatively infrequently and was never the predominant wound inhabitant. No patient treated with cerium developed a necrotizing wound infection. Analysis of the initial bacteriological data indicated that, in contrast to previous results using the nitrate or sulfadiazine salts of silver, when Gram-negative species predominated, the flora when cerium was used tended to be predominately composed of Gram-positive species. Some patients were therefore treated simultaneously with cerium nitrate and silver sulfadiazine; this to date has resulted in an even more efficient suppression of the wound flora than had been previously observed using either cerium alone or silver salts alone; preliminary results using the simultaneous topical therapy in patients with injuries that previously were uniformly lethal have been excellent.

No toxicity attributable to the use of cerium was observed, although one instance of methemoglobinemia due to nitrate was documented. The use of cerium nitrate was associated with a nearly 50 percent reduction in the anticipated death rate. It is plain that cerium nitrate is a promising new topical antiseptic agent for the treatment of burns, particularly when used in combination with silver sulfadiazine.

In the practices of this invention as described hereinabove, the cerium compound cerium nitrate, particularly cerous nitrate hexahydrate $Ce(NO_3)_3 \cdot 6H_2O$, has been employed. This cerium compound is readily available in substantially chemically pure form. Other cerium compounds, however, are equally useful in the practices of this invention. Preferably, the cerium compounds employed should be capable of possessing or exhibiting solubility in aqueous solutions, such as water-solubility of at least about 0.01M. In practice, however, even the slightly soluble cerium compounds or cerium salts which exhibit slight solubility or a solubility below 0.01M at about room temperature, e.g. in the range 15°-25° C., to provide an aqueous solution having a concentration of at least about 0.001M, are also useful. Cerium compounds which are useful in the practice of this invention in addition to cerous nitrate include cerous acetate and its hydrate, cerous chloride, cerium nitrate, basic, $Ce(OH)(NO_3)_3 \cdot 3H_2O$, cerous sulfate, cerous bromate $Ce(BrO_3)_3 \cdot 9H_2O$, cerous bromide $CeBr_3 \cdot H_2O$, the cerium iodates $Ce(IO_3)_3 \cdot 2H_2O$ and $Ce(IO_3)_4$, slightly soluble cerium compounds, cerous iodide $CeI_3 \cdot 9H_2O$, cerous chloride $CeCl_3$, cerium sulfate $Ce(SO_4)_2$ which forms basic salts and cerous oxalate $Ce(C_2O_4)_3 \cdot 9H_2O$. It is preferred in the practices of this invention, however, to employ the cerium compound cerous nitrate. In general, however, any physiologically acceptable salt or compound of cerium, particularly cerium salts, are suitable in the practices of this invention.

The cerium compound or salt employed in compositions and in the burn treatment or therapy in accordance with this invention is present and/or employed in an effective bacteriostatic or antibacterial amount. As indicated hereinabove, it is preferred that the concentration of the cerium compound in the cerium-containing compositions in accordance with this invention be at least about 0.01M, more or less, such as in the range 0.02M to about 0.2M.

The burn therapy in accordance with this invention, as indicated hereinabove, might also involve the application of silver sulfadiazine to the burn surface. In the combination therapy including both a cerium compound, such as cerous nitrate, and silver sulfadiazine, the cerium compound and silver sulfadiazine may be employed separately or in combination. In one embodiment of the invention the cerium compound, preferably dissolved in an aqueous solution thereof, is applied to the burn wound surface followed by the application of silver sulfadiazine, preferably dispersed in a water-soluble or water-dispersible hydrophilic cream. In another embodiment the silver sulfadiazine may first be applied to the burn wound followed by the application of the cerium compound in a suitable carrier, such as an aqueous solution thereof or an aqueous solution thereof dispersed in a water-dispersible or water-soluble hydrophilic cream. Preferably, in the combination therapy involving both a cerium compound and silver sulfadiazine, the cerium compound in the form of an aqueous solution thereof and silver sulfadiazine as finely divided solid particles are dispersed or emulsified in a water-dispersible or water-soluble hydrophilic carrier or cream, such as an oil-in-water emulsion carrier or cream.

Compositions in accordance with this invention containing a cerium compound or a cerium compound and silver sulfadiazine dispersed in a water-dispersible hydrophilic carrier or ointment, e.g. a hydrophilic oil-in-water emulsion, may be characterized by the following components and percentages by weight set forth in accompanying Table II:

TABLE II

| Component | % By Weight |
|---|---|
| Petrolatum | 0–25 |
| Water-insoluble $C_{16}$–$C_{22}$ fatty alcohol | 7–45 |
| Emollient | 0–15 |
| Emulsifying Agents, preferably non-ionic | 4–16 |
| Humectant | 7–40 |
| Silver Sulfadiazine | 0.1–10 |
| Preservative | 0–0.3 |
| Deionized or Distilled Water q.s. | 100 |
| Cerium Compound | 0.05–4 |

The fatty alcohols, stearyl alcohol, cetyl alcohol, lauryl alcohol and myristyl alcohol are useful in the preparation of compositions in accordance with this invention. These preferential oil-soluble fatty alcohols act as a stiffener in the resulting composition. As the emollient, isopropyl myristate, lanolin, lanolin derivatives, isopropyl palmitate, isopropyl stearate and the corresponding sebacates and other known emollients are suitable. As the emulsifying agent sorbitan monooleate, such as an amount in the range 0.5–4 percent by weight, and polyoxyl 40 stearate in an amount in the range 7–12 percent by weight, both non-ionic emulsifying agents are satisfactory. A suitable humectant would be propylene glycol, sorbitol or glycerin and mixtures thereof, all being water-soluble compounds. A suitable preservative would be any of the useful conventional water-soluble preservatives which exhibit anti-microbial activity, such as sorbic acid, benzoic methylparaben and propylparaben and mixtures thereof.

In the formulation of a cerium compound or a cerium compound and a silver sulfadiazine-containing composition having the composition set forth in Table II hereinabove, as the amount of aqueous phase is increased, the solid content, i.e. the water-immiscible or water-insoluble components, e.g. fatty alcohol, such as stearyl alcohol, and/or petrolatum, must also be increased relatively to help stiffen the composition. The preservative, e.g. methylparaben, is employed in the formulation only as a preservative for the overall composition and, as indicated, methylparaben was found to be a satisfactory preservative. Methylparaben, as indicated, however, may also be used in combination with propylparaben.

Accordingly, compositions useful in the practices of this invention would include compositions comprising 0–25 percent by weight petrolatum, 7–45 percent by weight stearyl alcohol, 0–15 percent by weight isopropyl myristate, 5–20 percent by weight of an emulsifying agent, 7–40 percent by weight propylene glycol, 0.5–10 percent by weight silver sulfadiazine and about 0.01–0.5M cerium compound in the resulting composition, the remainder being water, as required to bring the total percentages to 100 percent. Other compositions useful would include compositions consisting essentially of 0.5–2 percent by weight silver sulfadiazine, 7–8 percent by weight propylene glycol, 38–44 percent by weight water, 14–18 percent by weight petrolatum, 14–18 percent by weight stearyl alcohol, 5–8 percent by weight isopropyl myristate, 0.5–2 percent by weight sorbitan monooleate and 6–10 percent by weight polyoxyl 40 stearate and 0.01–4% by weight cerium compound. Another composition useful in the practice of this invention would include the composition consisting essentially of 0–25 percent by weight petrolatum, 7–45 percent by weight of an aliphatic fatty alcohol having a carbon atom content in the range $C_{16}$–$C_{22}$, 0–15 percent by weight of an emollient, 7–16 percent by weight of an emulsifying agent, 7–14 percent by weight of a humectant, 0.2–10 percent by weight silver sulfadiazine and 0.1–2% by weight cerium compound.

The following hydrophilic or oil-in-water emulsion bases are available and suitable in the preparation of compositions in accordance with this invention: Neobase manufactured by Burroughs-Wellcome, Unibase manufactured by Parke-Davis, Emulsion Base manufactured by Almay, Dermabase manufactured by Marcelle, Cetaphil manufactured by Texas Pharmacal. In general, hydrophilic bases, such as hydrophilic bases of the oil-in-water emulsion type, are characterized by the ease which they may be removed from the skin by washing with water.

As will be apparent to those skilled in the art in the light of the foregoing disclosure, many alterations and modifications are possible in the practice of this invention without departing from the spirit or scope thereof.

I claim:

1. A method of treating burns which comprises applying to the burn surface a composition comprising an effective anti-bacterial amount of an admixture of cerous nitrate and silver sulfadiazine, said composition being a semi-soft or cream-like, water-dispersible hydrophilic composition and containing said admixture therein as a dispersion or emulsion, said cerous nitrate being present in said composition in an amount in the range 0.05–4% by weight and said silver sulfadiazine being present in said composition in an amount in the range 0.1–10% by weight.

2. A method of treating burns in accordance with claim 1 wherein said cerous nitrate is present in said composition as an aqueous solution of cerous nitrate.

3. A composition useful in burn therapy comprising an effective anti-bacterial amount of an admixture of cerous nitrate and silver sulfadiazine, said composition being a semi-soft or cream-like, water-dispersible hydrophilic composition containing said admixture as a dispersion or emulsion therein, said cerous nitrate being present in said composition in an amount in the range 0.05–4% by weight and containing silver sulfadiazine therein in an amount 0.1–10% by weight.

4. A composition in accordance with claim 3 wherein said cerous nitrate is present in said composition as an aqueous solution of cerous nitrate.

5. A method of treating burns in accordance with claim 1 wherein said semi-soft or cream-like, water-dispersible hydrophilic composition comprises an oil-in-water emulsion.

6. A composition in accordance with claim 3 wherein said semi-soft or cream-like, water-dispersible hydrophilic composition comprises an oil-in-water emulsion.

* * * * *